United States Patent [19]

Lehnert et al.

[11] Patent Number: 5,065,613

[45] Date of Patent: Nov. 19, 1991

[54] METHOD FOR THE DIRECT PRESENTATION OF A DIFFERENTIAL MEASURED QUANTITY IN TERMS OF ITS CORRECT PHYSICAL UNIT

[75] Inventors: Michael Lehnert, Rodenbach; Ulrich Modlinski, Alzenau-Albstadt; Rudi Roess, Bruchkoebel, all of Fed. Rep. of Germany

[73] Assignee: Rosemount GmbH & Co., Fed. Rep. of Germany

[21] Appl. No.: 495,101

[22] Filed: Mar. 19, 1990

[30] Foreign Application Priority Data

Dec. 5, 1989 [DE] Fed. Rep. of Germany ....... 3940141

[51] Int. Cl.$^5$ ............................................... G01N 7/00
[52] U.S. Cl. .................................. 73/23.2; 73/23.21; 422/83; 340/632; 340/634
[58] Field of Search ................. 73/23.2, 23.21; 422/83; 340/632, 634

[56] References Cited

U.S. PATENT DOCUMENTS

| | | | |
|---|---|---|---|
| 4,101,221 | 7/1978 | Schunck et al. | 356/205 |
| 4,351,181 | 9/1982 | Currans | 73/23.21 |
| 4,488,811 | 12/1984 | Fukuma | 356/319 |
| 4,526,028 | 7/1985 | Hübner | 340/632 |
| 4,578,762 | 3/1986 | Wong | 422/83 |
| 4,709,575 | 12/1987 | Myers | 73/23.2 |

FOREIGN PATENT DOCUMENTS

| | | |
|---|---|---|
| 3116344 | 11/1982 | Fed. Rep. of Germany . |
| 3707100 | 9/1988 | Fed. Rep. of Germany . |
| 3804486 | 8/1989 | Fed. Rep. of Germany . |
| 219584 | 6/1985 | German Democratic Rep. . |
| 979850 | 5/1961 | United Kingdom . |
| 2009545 | 11/1978 | United Kingdom . |
| 2175392 | 4/1986 | United Kingdom . |

Primary Examiner—Tom Noland
Assistant Examiner—W. Francos
Attorney, Agent, or Firm—Hill, Van Santen, Steadman & Simpson

[57] ABSTRACT

A method for the direct presentation of a differential measured quantity, in particular, a differential gas concentration measurement, in terms of its correct physical unit is disclosed. A characteristic curve representing the output of a gas sensor detector as a function of gas concentration is obtained in an absolute coordinate system. A reference level at which the differential measurement is to occur is defined on this characteristic curve by a defined input or, respectively, output value. This reference level defines the origin of a differential coordinate system from which the differential measurement may be directly ascertained.

5 Claims, 1 Drawing Sheet

METHOD FOR THE DIRECT PRESENTATION OF A DIFFERENTIAL MEASURED QUANTITY IN TERMS OF ITS CORRECT PHYSICAL UNIT

FIELD OF THE INVENTION

The present invention is directed to a method for the direct presentation of a differential measured quantity in terms of its correct physical unit where there is a non-linear relationship between the input quantity and the output quantity. The "differential measured quantity" is the output value of a differential measurement made by a measuring instrument, in particular, a gas analyzer. However, the present invention can also be employed in measuring methods wherein physical, chemical or electrical quantities are to be determined.

BACKGROUND OF THE INVENTION

Many measuring methods for the acquisition of physical, chemical or electrical quantities have a non-linear relationship between the measured quantity (the output value of the measuring instrument, i.e., an opto-electronic detector) and the measured signal (the input value at the measuring instrument, i.e. the quantity to be measured). In the measuring methods employed in gas analysis, it is frequently not the absolute value of the gas concentration which is determined. Rather, it is the difference in gas concentrations between a reference gas and the measured gas which is identified. Thus, the identification of the differences in gas concentration plays a significant role in the field of opto-electronic gas analysis.

Non-dispersive gas analyzers are typically designed for the measurement of a permanently selected gas component. The concentration of the gas under measurement is identified by the transmissivity of an infrared light beam as it is beamed through the gas path. Such opto-electronic measuring methods and measuring instruments are described, for example, in brochure number 43-500.01 of Leybold AG. In particular, FIG. 2 on page 2 of the brochure explains the measuring principle of an infrared gas analyzer.

An infrared gas analyzer can primarily be divided into two integrated physical sections. The first section is the measurement side which contains the gas under measurement. The second section is the comparison side which is normally filled with nitrogen and closed in a gas-tight fashion.

Both the measurement side and comparison side are transirradiated with infrared light. An amount of infrared light is absorbed by the gas under measurement, this amount being dependent on the concentration of the gas and occurring within the infrared spectral range. A light chopper wheel that turns at a specified RPM (i.e. 1600 RPM) produces light pulses corresponding to the measurement and comparison beams which transirradiate the measurement and comparison sides respectively. An intensity difference is thereby produced between the beams which corresponds to the concentration difference between the gas under measurement and the comparison gas.

The infrared light pulses which proceed through the measurement side and comparison side impinge an infrared detector which is designationally adjustable to receive a single wavelength range. The output of the detector is supplied to a signal processing means or some other form of electronic evaluator.

There is a non-linear relationship between the infrared detector output and the gas concentration. FIG. 1 illustrates this non-linear relationship. In FIG. 1 the abscissa 10 represents the gas concentration values. The detector output values are represented by the ordinate 11. The non-linear curve 9 represents the relationship between the gas concentration and the output value of the detector. This non-linear curve 9 can be described by the Lambert-Beer Law where the infrared detector is used in an absorption photometer such as described above.

The program line 12 represents the rated line. As with most non-linear devices, the stated object is to correct the non-linear actual curve 9 into the linear rated line 12.

Correction of the curve can take place in several different manners. First, the correction can be carried out within a linearization circuit. Additionally, computers may be used to undertake the correction with the assistance of installed EDP programs. Finally, comparison tables may be used to correct the actual curve 9 into the rated curve 12.

In addition to the absolute identification of the measured quantity, it is of particular importance to obtain the difference between the two absolute quantities. However, the above-described methods for correcting the actual curve into the rated curve cannot be employed when performing a differential measurement. This is due to the fact that different measured signal voltages and curve curvatures derive for an arbitrary but fixed range of differences between the measured quantities, dependent on the underlying reference level.

There are two methods currently employed for calculating the differential measurements. In the first method, the absolute values of the two measured quantities are first ascertained. These two absolute values are subsequently subtracted to determine the difference measurement.

This first method, however, has several disadvantages. It requires exceptional accuracy and precision of the absolute values since the difference to be measured is small when compared to the absolute values. Additionally, this method is disadvantaged in that the two absolute measured quantities must be identified independent of one another. Consequently, any differential value calculated from the two independently measured absolute quantities contains the imprecisions present in two separate measurements.

It also known to employ a method for direct formation of the differences. In such a method, the differential value to be identified must be acquired based on two separate characteristic curves since the influence of the reference level on the measured signal must also be taken into consideration as well as the linearization of the differential measurement. This gives rise to a characteristics field. To this end, the reference level is identified with its own absolute measurement and associated linearization. In order to meet the high precision demands made of the differential measurement, paired testing and balancing agents are usually employed.

When the above-noted methods are employed, the actual range of differential measurements are generally presented without linearization since the influence of the reference level on the linearity of the measured values can only be corrected with great difficulty and an extensive outlay of equipment.

SUMMARY OF THE INVENTION

A method for obtaining a direct display of physical quantities is set forth wherein a direct identification of absolute values and differential values is obtained. Employment of the method eliminates the need to undertake a calibration for differential measurements. Furthermore, employment of the inventive method eliminates the need to provide test agents in a paired execution and, further, reduces measurement errors.

The present method is particularly directed to nondispersive photometry gas analysis employing optoelectronic gas analyzers that generate light pulses of different intensities from measurement beams and comparison light beams, the intensity difference corresponding to the concentration difference between a gas under measurement and a comparison gas. In such a gas analyzer, a characteristic curve is recorded in an absolute coordinate system which represents the absolute output value of the sensor as a function of the absolute input value. A reference level is defined on this characteristic curve by a defined input value or, respectively, output value, whereat the concentration difference measurement between the gas under measurement and the comparison gas is to occur. This reference level defines the origin of a differential coordinate system in which the differential measurement may be directly determined.

The method of the invention is particularly advantageous when used to present the difference between the concentrations of two gases since, as previously noted, it is not the absolute values of gas concentrations but the differences in gas concentrations that are identified in the measuring methods of gas analyzers.

BRIEF DESCRIPTION OF THE DRAWINGS

Other objects, features, and advantages of the invention will best be understood from the following detailed description, taken in conjunction with the accompanying drawings, of which.

DESCRIPTION OF THE PREFERRED EMBODIMENT

Figure 1:
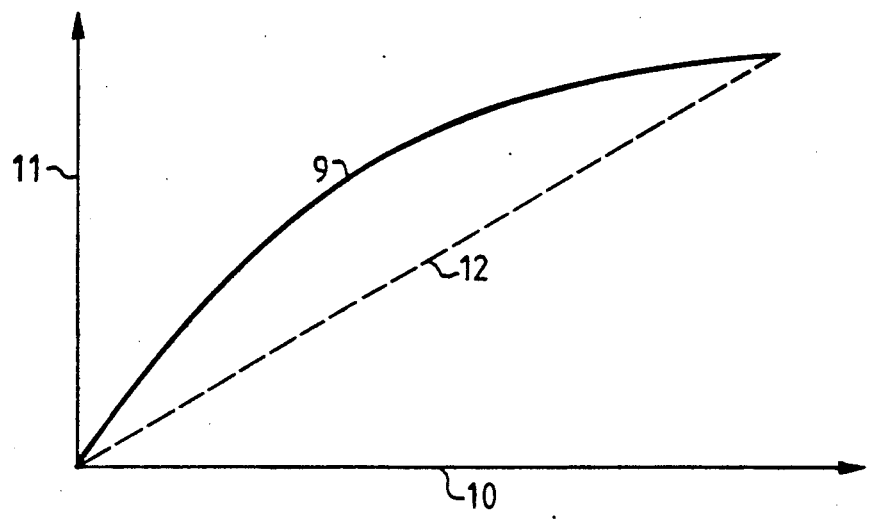
FIG. 1 illustrates the non-linear relationship which exists between gas concentration and the detector in an opto-electronic gas analyzer.
Figure 2:
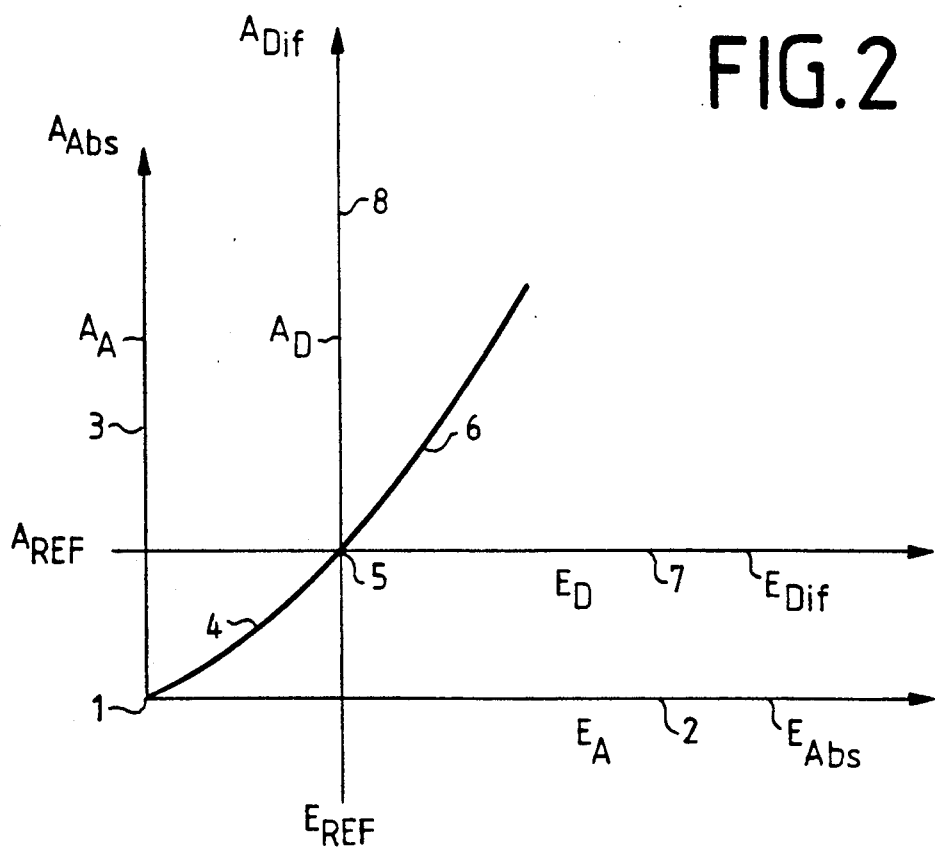
FIG. 2 is a graphical illustration of the method as it is to be employed in an opto-electronic gas analyzer.

As shown in FIG. 2, a characteristic curve comprising portions 4 and 6 is first ascertained in an absolute coordinate system. This characteristic curve describes the relationship between the input values E (signal output of the detector) and output values A (gas concentration). The characteristic curve 4,6 is standardized in the appropriate physical unit.

The characteristic curve is acquired by obtaining a series of absolute measurements at different points (i.e., different gas concentrations or, alternatively, different detector outputs). Mathematical approximation techniques such as, for example, parabolic interpolation using the LaGrange method, are used to plot the characteristic curve based on the measurements taken at the different points.

Any linearization of the absolute value is also utilized for differential measurements. To this end, the absolute level at which the differential measurement occurs is first measured, the absolute value defining a reference point. The origin of a differential coordinate system is then transformed into this reference point. Thus, it is important that the scalings of both coordinate systems (the absolute coordinate system and the differential coordinate system) are the same so that a correct measurement will be obtained.

Differential measurements are usually more sensitive than absolute measurements. Consequently, any absolute measurement should be adapted to the more sensitive differential scaling by amplifying the absolute measurement with a specified gain.

As shown in FIG. 2, the absolute coordinate system has its origin at 1. The units for the absolute input values EA at the measuring instrument are entered on the abscissa 2 of the absolute coordinate system. The ordinate 3 represents the absolute output values AA of the measuring instrument. As previously noted the characteristic curve 4,6 represents the dependency of the output values on the input values.

A reference point 5 is ascertained on the characteristic curve 4,6 and is defined by a specific input value EREF or, respectively, by a specific output value AREF. Point 5 defines the origin of the differential coordinate system having the abscissa 7 and the ordinate 8. It is point 5 which represents the reference level from which the differential measurement is to be taken.

In the differential coordinate system, the abscissa 7 represents the input value of the differential measurement (the output of the detector). The ordinate 8 of the differential coordinate system represents the output values of the differential measurement AD (the differential gas concentration). The second portion of the characteristic curve 6 is thus the presentation of the output value AD of a differential measurement as a function of the input value ED. As a result, the gas concentration differential can be ascertained directly in the differential coordinate system while an absolute measurement may be directly obtained in the absolute coordinate system.

After the respective coordinate systems have been defined and the characteristic curve has been ascertained, the following relationship exists between the linearized measured value of the differential measurement:

$AD = AE - AREF$
$AA = f(EA) = f(EREF + ED)$
$AREF = f(EREF)$.

Any influence which the reference level has on the sensitivity of the differential measurement is automatically corrected by the "shifting" of the differential coordinate system on the characteristic curve. Moreover, a correct linearization also occurs in the differential measurement and, as a result, a linear measured value is thus present. Consequently, it is only the absolute measurement which must be calibrated since, after matching the scaling (this is omitted given constant gain), the differential measurement is automatically calibrated.

Expressed in simplified terms, the differential measurement is evaluated by scaling matching and addition of the reference level as an absolute measurement on the characteristic curve. The absolute measured quantity of the differential measurement belonging to the reference level is subsequently acquired through subtraction.

The method of the invention may be readily employed using standard electronic components within the gas analyzer. In such a gas analyzer, an absolute measurement with a detector that supplies the output value U1 (typically in the form of a measurement voltage) is ascertained that corresponds to the input value $C_1$ (i.e., $C_1 = 340$ ppm). Next, a differential measurement is obtained using a detector that supplies the output value U2 (also in the form of a measurement voltage). The gas concentration $C_1$ is one of the two concentrations to be compared.

An arithmetic unit may be used to add the second output value U2 to the first input value U1 to arrive at the sum U3, the sum U3 corresponding to an input value $C_2$ (i.e., a gas concentration of $C_2 = 350$ ppm). The arithmetic unit then subtracts the concentration $C_1$ (which has been stored in a memory) from the identified measured value $C_2$ to obtain a differential measurement value C (10 ppm in the present example).

A number of advantages are obtained as a result of employing the method of the invention. First, a direct indication of the absolute values and differential values may be obtained. Second, there is no need for the calibration of the differential measurement. Third, there is no further need to employ test agents in paired execution. Finally, measuring errors are reduced since only one characteristic curve has to be interpreted and ascertained.

Although modifications and changes may be suggested by those skilled in the art, it is the intention of the inventor to embody within the patent warranted hereon all changes and modifications as reasonably and properly come within the scope of his contribution to the art.

I claim:

1. A method for obtaining the direct measurement of a differential gas concentration in a gas analyzer comprising the steps of:

measuring a detector output signal at a plurality of levels respectively corresponding to a plurality of input gas concentrations, said detector having a non-linear relationship between said plurality of levels and said plurality of input gas concentrations;

plotting a characteristic curve in an absolute coordinate system based on said plurality of detector output signals and said plurality of input gas concentrations, said absolute coordinate system having a defined scaling;

defining a reference value on said characteristic curve, said reference value corresponding to a level at which a differential gas measurement is to take place;

using said reference value as an origin of a differential coordinate system, said differential coordinate system having a scaling equal to said scaling of said absolute coordinate system;

measuring a concentration of a gas to be measured using said detector, said detector having an output level corresponding to said concentration of said gas to be measured;

locating said output level along said characteristic curve;

directly ascertaining a differential measurement value in said differential coordinate system based on said output level located on said characteristic curve;

displaying said differential measurement value on said gas analyzer.

2. A method for obtaining a direct measurement of a differential gas concentration as recited in claim 1, further comprising the step of linearizing said characteristic curve.

3. A method for obtaining a direct measurement of a differential gas concentration as recited in claim 1, wherein said step of plotting a characteristic curve in an absolute coordinate system based on said plurality of levels and said plurality of gas concentrations is further defined by plotting a characteristic curve in an absolute coordinate system based on said plurality of levels and said plurality of gas concentrations using a LaGrange method for parabolic interpolation.

4. A method for obtaining the direct measurement of a differential gas concentration value in a gas analyzer comprising the steps of:

obtaining an absolute measurement with a detector, said detector having a first output signal level corresponding to a first gas concentration value;

obtaining a differential measurement with said detector, said detector having a second output signal level;

adding said first output signal level to said second output signal level in an arithmetic unit to obtain an output sum, said output sum corresponding to a second gas concentration value;

subtracting said second gas concentration value from said first gas concentration value to obtain said differential gas concentration value; and, displaying said gas concentration value on said gas analyzer.

5. A method for the direct presentation of a differential gas measurement, comprising the steps of:

recording a characteristic curve in a first coordinate system, said characteristic curve representing a dependency between absolute output values of a detector and gas concentrations;

defining a reference value on said characteristic curve, said reference value corresponding to a level at which a differential gas measurement between a gas under measurement and a comparison gas is to take place, said reference value defining an origin of a second coordinate system.

* * * * *